US010104896B2

(12) United States Patent
Benavides et al.

(10) Patent No.: US 10,104,896 B2
(45) Date of Patent: Oct. 23, 2018

(54) COMBINATION OF BIOLOGICAL PESTICIDES

(71) Applicants: FEDERACIÓN NACIONAL DE CAFETEROS DE COLOMBIA, Bogotá (CO); ECOFLORA AGRO S.A.S., Rionegro (CO)

(72) Inventors: Pablo Benavides, Bogotá (CO); Carmenza Góngora, Bogotá (CO)

(73) Assignee: Federacion Nacional de Cafeteros de Colombia, Bogota (CO)

( * ) Notice: Subject to any disclaimer, the term of this patent is extended or adjusted under 35 U.S.C. 154(b) by 167 days.

(21) Appl. No.: 14/762,213

(22) PCT Filed: Nov. 29, 2013

(86) PCT No.: PCT/IB2013/060525
§ 371 (c)(1),
(2) Date: Jul. 21, 2015

(87) PCT Pub. No.: WO2014/111764
PCT Pub. Date: Jul. 24, 2014

(65) Prior Publication Data
US 2015/0359229 A1 Dec. 17, 2015

(30) Foreign Application Priority Data
Jan. 21, 2013 (CO) ................... 13-010500

(51) Int. Cl.
A01N 63/04 (2006.01)
A01N 65/38 (2009.01)
A01N 65/42 (2009.01)
A01N 65/00 (2009.01)

(52) U.S. Cl.
CPC ............ *A01N 63/04* (2013.01); *A01N 65/00* (2013.01); *A01N 65/38* (2013.01); *A01N 65/42* (2013.01)

(58) Field of Classification Search
None
See application file for complete search history.

(56) References Cited

FOREIGN PATENT DOCUMENTS

CN     1500392 A  *  6/2004  ............. A01N 65/00

OTHER PUBLICATIONS

Ecoflora Agro, CapsiAlil®, Accessed Jun. 14, 2018, Available online at: ecofloragro.com/capsialil-2/.*
Grant Notification—Colombian Patent Application 13-010500.
Capsialil Material Safety Data Sheet, EcoFlora Agro, Aug. 23, 2012.
Compatibility between Bauveria Bassiana and Metarhizium anisopliae with Nimkol-L in the control of Heterimtermes tenius, Castigliori et al., Manejo Integrado de Plaga y Agroecologia No. 69 p. 38-44 (2003).
Use of Entomopathogenic Fungi in Latin America, Alves et al., Advances in Microbial Control of Insext Pests, p. 193-211 (2002).
Eficacia De Mezclas De Cepas Del Hongo Beauveria bassiana En El Control De La Broca Del Café, Cardenas, et. al., Cenicafe, 58(4):293-303 (2007).
Effect of the toxin beauvericin on Hypothenemus hampei; Arboleda et al., Manejo Integrado de Plagas y Agroecología (Costa Rica) No. 68 p. 71-76, (2003).
Cytotoxic Activity of Fungal Metabolites from the Pathogenic Fungus Beauveria bassiana: An Intraspecific Evaluation of Beauvericin Productio; Arboleda et al., Curr. Microbiol. 63:306-312 (2011).
Attachment of Mycopathogens to Cuticle. The Initial Event of Mycoses in Arthropod Hosts; Boucias et al., Spore Attachment and Invasion (1991).
El manejo de cafetales y su relacion con el control de la broca del café en Colombia, Alex Enrique Bustillo Pardey, (2007).
Brocarta, Boletin Informativo sobre la broca del Cafe, Bustillo, No. 37 (Jan. 2004).
El Desarrollo y uso de entomopatogenos para el control de la broca de cafe, Bustillo, p. 70-85 (1998).
Eficacia de mezclas de cepas de Beauveria bassiana para control de la broca del cafe, Hypothenemus hampei, Cardenas et al., (Abstract) XXXIV Congreso, Sociedad Colombiana de Entomologia, (2007).
Exploiting the genetic diversity of Beauveria bassiana for improving the biological control of the coffee berry borer through the use of strain mixtures, Cruz et al., Appl. Microbiol. Biotechnol. 71:918-926 (2006).
Microbial Control of Insect Pests With Entomopathogenic Fungi in China: A Decade's Progress in Research and Utilization; Ming-Guang Feng, Advances in Microbiol. Control of Insect Pests, 213-234 (2002).
Production, Formulation and Application of the Entomopathogenic Fungus *Beauveria bassiana* for Insect Control: Current Status; Review Article; Feng et al., Biocontrol Science and Tech. 4:3-34 (1994).
Variation in gene expression patterns as the insect pathogen Metarhizium anisopliae adapts to different host cuticles on nutrient deprivation in vitro, Freimoser et al., Microbiology, 151:361-371 (2005).
The Use of Entomogenous Fungi for Pest Control and the Role of Toxins in Pathogenesis; Gillespi and Claydon, Pstic. Sci. 27:203-2015 (1989).
Entomopathogenic Fungi and Their Role in Regulatio of Insect Populations; Goettel et al.; Comprehensive Molecular Insect Science, vol. 6. pp. 361-406 (Edited by Lawrencel. Gilbert, Kostad Iantrou and Sarjeet S. Gill., Elsevier, Boston (2005).

(Continued)

*Primary Examiner* — Jennifer M. H. Tichy
(74) *Attorney, Agent, or Firm* — The Morales Law Firm; Joseph L. Morales

(57) ABSTRACT

The present invention relates to a natural pesticide formulation containing: A) botanical products having an arthropod repellent effect (preferably mixture of garlic and chili oils) and B) an entomopathogenic fungus strain or a blend of entomopathogenic fungi strains specific for said arthropod control (preferably blend of *Beauveria bassiana* strains). The formulation is useful in the control of coffee berry borer (*Hypothenemus hampei*) in coffee plants and of other important insects in corn crop fields and green-house crop fields (flowers and vegetables).

9 Claims, 1 Drawing Sheet

(56) References Cited

OTHER PUBLICATIONS

Transformation of Beauveria bassiana strain Bb9112 with the genes from green fluorescent protein and the pretease prlA of Metarhizium anisopliae, Gongora, Carmenza E., Rev. Colomb. Entomol. 30(1), p. 15-21 (2004).
Captitulo 9, Los hongos entomotpatogenos en el control de insectos, Gongora, Carmenza E., Los Insectos y Su Manejo en la Caficultura Colombiana, 133-149 (2008).
Approaches to and Successes in Developing Transgenically Enhanced Mycoherbicides; Gressel et al., Novel Biotechnologies for Biocontrol Agent Enhancement and Management, 297-305 (2007).
Orchard Applications; Sapiro-Ilan et al., Nematodes as Biocontrol Agents 215-229 (2005).
Interactions Between Fungal Pathogens and Insect Hosts, Hajek and Leger, Annu. Rev. Entomol. 39:293-322 (1994).
Use of Pathogen Combinations to Overcome the Constraints of Temperature on Entomopathogenic Hyphomycetes against Grasshoppers, Inglis et al., Biological Control 8:143-152 (1997).
Evaluación y validación de mezclas de Beauveria bassiana (Balsamo) Vuillemin y Metarhizium anisopliae (Metschnikoff) Sorokin para el control de la broca del café en frutos infestados caídos al suelo, Jorge Luis Jaramillo Gonzalez, Thesis, Universidad Nacional de Colombia (2012).
Bassianolide, a New Insecticidal Cyclodepsipeptide from Beauveria bassiana and Verticillium lecanii, Kanaoka et al., Agric. Biol. Chem 42(3):629-635 (1978).
The Role of Destruxins in the Pathogenicity of Metarhizium anisopliae for Three Species of Insect; Kershaw et al., J. of Invertebrate Path. 74:213-223 (1999).
Researchgate, Conversation Transcript, Saito Rachel (Nov. 15, 2012).
The Coffee Berry Borer, Coleoptera Scolytidae, Pest of Coffee, pp. 114-149 (London, Longman, Green and Co 1968).
Combined Effect of Beauveria Bassiana With Neem on Virulence of Insect in Case of Two Application Approaches; Islam and Omar, J. Anim. Plant. Sci. 22(1):77-82 (2012).
Synergistic Effect of Imidacloprid and Two Entomopathogenic Fungi on the Behavior and Survival of Larvae of Diaprepes abbreviatus (Coleoptera: Curculionidae) in Soil, Quintela and McCoy, J. Biol. and Microbial Control 91(1):110-122 (1998).
Biologia de Hypothenemus hampei (Ferrari) en frutos de cafe de diferentes edades; Montoya and Murillo, Cenicafe 45(1):5-13 (1994).
Laboratory and greenhouse evaluation of the entomopathogenic fungi and garlic-pepper extract on the predatory mites, *Phytoseiulus persimilis* and *Neoseiulus californicus* and their effect on the spider mite *Tetranychus urticae*, Vergel et al., Biol. Control 57:143-149 (2011).

Phylogenetic origins of African and Neotropical Beauveria bassiana s.l. pathogens of the coffee berry borer, Hypothenemus hampei, Rehner et al., J. of Invert. Pathol. 93:11-21 (2006).
Synergism—a Patent View; Richer, David L., Pest. Sci. 19:309-315 (1987).
Transformación de Beauveria bassiana Bb9205 con genes prlA, prlJ y ste1 de Metarhizium anisopliae y evaluación de su patogenicidad sobre la broca del café, Rodriguez and Gongora, Rev. Col. de Entomologia 31(1):51-58 (2005).
Definitions of pathogenicity and virulence in invertebrate pathology; Shapiro-Ilan et al., J. Invert. Pathol. 88:1-7 (2005).
Construction of an improved mycoinsecticide overexpressing a toxic protease, Leger et al., Proc. Natl. Acad. Sci. 93:6349-54(1996).
Prepenetration Events during Infection of Host Cuticle by Metarhizium anisopliae; Leger et al., J. of Invert. Pathol. 58:168-79 (1991).
World-wide distribution of genetic variation among isolates of *Beauveria* spp.; Leger et al., Mycol. Res. 96(12):1007-15 (1992).
Laboratory and greenhouse evaluation of the entomopathogenic fungi and garlic-pepper extract on the predatory mites, *Phytoseiulus persimilis* and *Neoseiulus californicus* and their effect on the spider mite *Tetranychus urticae*; Biol. Control 57:143-49 (2011).
Insect Pathology, Chapter 10 Fungal Infections; Subdivision Deuteromycotina, Yoshinori Tanada and Harry K. Kaya, pp. 358-361 (1992).
Registro e Identificacion de Beauveria bassiana en Hypothernemus hampei en Ancuya, Departamento de Narino, Colombia, Velez-Arango and Benavides-Gomez; Cenicafe 41(2):50-57 (1990).
Evaluation of Beauveria bassiana (Ascomycota: Hypocreales) as a control of the coffee berry borer Hypothenemus hampei (Coleoptera: Curculionidae: Scolytinae) emerging from fallen, infested coffee berries on the ground, Vera et al., Biocontrol Science and Technology 21(1):1-14 (2011).
Evaluacion de insecticidas para el control de la broca del cafe en Colombia, Villalba-Gauli et al., Cenicafe 46(3):152-63 (1995).
Certificate of Biological Deposit and Listing—Jun. 9, 2016.
Ecoflora Internal Manufacturing Protocol—Unpublished.
Evaluation of the Synergistic Effect of Botanical Extracts of Garlic and Wormwood and a Mixture of Three Strains of Entomopathogenic Fungus *Beauveria bassiana* (Bb9001, Bb9024, Bb9119) on the Mortality of the Coffee Berry Borer—Unpublished.
Patricia E. Vélez-Arango, et al., Characterization of Beauveria bassiana Isolates for the Control of Coffee Berry Borer, Integrated Pest Management (Costa Rica) 63:38-53 (2001).
Webpage Printout of Colombian National Registry for Biological Deposits—Aug. 17, 2017.

* cited by examiner

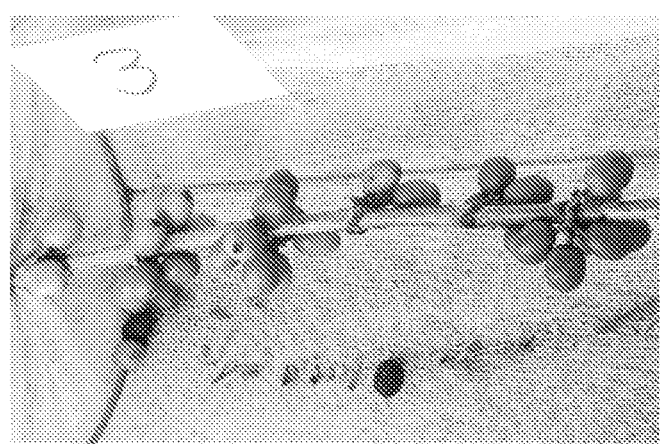
A
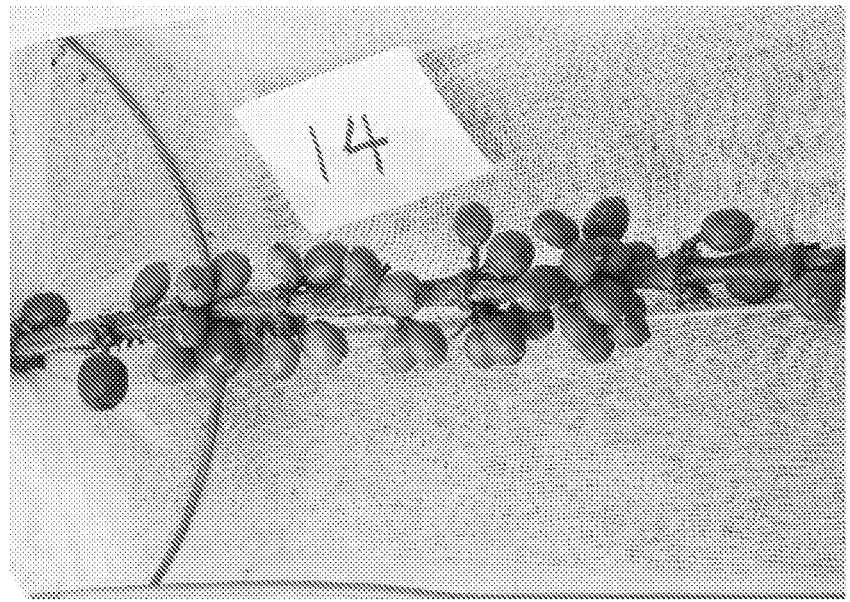
B

COMBINATION OF BIOLOGICAL PESTICIDES

1. FIELD OF THE INVENTION

The instant invention refers to alternative methodologies, especially in regards to repellent substance combinations and biological control such as entomopathogenic fungi, for arthropod pest control, such as lepidoptera pests such as *spodoptera*, homopetera such as the whitefly, and coleopteran (beetles) such as the coffee berry borer *Hypothenemus hampei*.

2. DESCRIPTION OF THE ART

Insects l are responsible for great losses in the agricultural sector in Colombia as well as worldwide. The development of insecticides through chemical synthesis in the 40's and 50's allowed farmers to solve phytosanitary problems and increase productivity, better known as the green revolution. However, continuous use of these molecules soon showed that their efficacy did not hold through time due to resistance insects would develop in the short term, which would then require from the industry new products to replace the existing ones. The above combined with environmental problems due to indiscriminate use of these products (pesticide toxic residues remaining on food crops, environmental alterations outside the treated zones, negative effects on non-target organisms, other insects surging and converting into pests and dangers to human health) led the scientific community to seek new alternatives for insect control better known as comprehensive management strategies and in lately as smart pest control.

CMP or comprehensive pest management is defined as "the use of a series of control measures (cultural, biological and chemical) which tends to reduce pest populations or pests affecting a crop field, at levels which cause no economic harm and which allow its production and marketing in a competitive manner. The control measures must be compatible and must not cause deleterious effects to nearby inhabitants nor nearby fauna, nor contaminate the agroecosystem" (NCA, 1969; Andrews and Quezada, 1989). From the above definition it is deduced that pest comprehensive management must use all available tools in order to face pests, such as cultural control practices, fostering beneficial fauna, and the introduction from their site of origin of biological enemies such as parasitoids and entomopathogens which play an important role in regulating pest populations. The term Crop Comprehensive Management (CCM) has recently been coined, considered a CMP wherein all crop agronomic management practices which are adverse to pest development are included.

Furthermore, smart pest control is based on the idea that insect control must be performed in such a way as to obtain the greatest sustainability with the least environmental impact. In other words, creating solutions based on biological and chemical agents with low toxicity wherein ethological knowledge and insect behavior are keys to its control, seeking economic and social benefit for farmers.

Taking into account these premises, biological control combined with the use of repellent substances which alter insect behavior and allow them to be in contact with the biocontrol agent longer, assuring the uptake of a greater dosage of the pathogenic agent, seems to be a novel strategy and quite appropriate for agricultural pest control. Below, possible biological control agents will be referenced as well as possible natural or botanical substances which may alter insect behavior due to a repellent activity and which may be used in these types of control strategies.

Biological controls are live organisms such as pathogens, parasitoids and predators, or products produced by these used to prevent or reduce losses or harm caused by pests.

Insect pathogens: these represent a group of microorganisms which, upon invading insects, have the ability to inflict disease. In general, the pathogenic microorganisms that invade and reproduce in the insect are termed entomopathogens. They are transmitted to insects by direct contact, ingestion and/or transmission from one generation to the next. Microorganisms which can cause disease in insects belong to entomovirus, bacteria, fungi, protozoan and entomonematode groups.

In general, control strategies look to use efficacious and economical controls. Hence, one of the more developed biocontrol groups until now correspond to the entomopathogen fungi group. Entomopathogenic fungi are eukaryote organisms, having a nucleus clearly defined by a membrane. They can be comprised of a single cell (unicellular), as in yeasts, or as in the majority of cases, they can be formed multicellularly through filamentous units known as hyphae, forming mycelium. Hyphae are formed by single-nucleate or multi-nucleate segments, separated by transverse walls.

Other natural-type insecticides are described in several patents. For example, US patent 2002/0031495 describes an active pesticide isolated from the *Beauveria bassiana* fungi, which may be used in agriculture, whose biomass contains a high proportion of spores, as well as preparation methods thereof. On the other hand, U.S. Pat. No. 5,631,276 teaches insecticide and acaricides comprising an effective quantity of endosulfan (A) in combination with the *Beauveria bassiana* fungi.

The first organisms identified as causing disease in insects were fungi, due to the fact it was possible to observe their growth in the insect's cuticle (Tanada and Kaya. 1993). Pathogenic fungi usually invade and multiply within insects, and diseases caused by them are coined mycosis. La majority of insect orders are susceptible to diseases caused by fungi, and they are particularly important for controlling coleoptera, given this order is especially resistant to virus and bacteria-borne diseases.

Entomopathogenic fungi are capable of causing disease in insects (Hajek, 2004), defining disease as an abnormal condition occurring in the insect due to physiological or physical disarrangements. Fungi pathogenicity is the condition of being pathogenic, i.e., having the capacity of inflicting disease in insects. On the other hand, virulence is the degree of pathogenicity, i.e., the amount of measureable disease that fungi can cause (Shapiro-Ilan et al., 2005). Virulence may also be determined by mortality due to a strain or mix of strains. Likewise, the degree of pathogenicity produced by a strain can be increased by mixing it with other strains. Therefore, it is possible that the strain combination which individually represent low virulence, may exhibit high virulence, as evidenced in later examples illustrated in the instant detailed description. For example, said fungi are associated to insects in all types of habitats, wherein water is included, ground and aerial parts of the plants (Hajek and St. Leger, 1994). More than 700 species of fungi exist reported as arthropod pathogens, and likewise play an important role in the regulation of insect population (Goettel et al., 2005).

A large diversity also exists with regards to its degree of speciation, and its range of adaptation extends from being compelling pathogens of some species (*Coelomomyces*) to being generalist organisms capable of infecting different host species, and even species that are facultative pathogens (*Metarhizium*). The epizootics caused by fungi are common in some insect species, whilst others rarely affected (Tanada y Kaya, 1993). Some of the entomopathogens, as in the case of *Beauveria bassiana*, may use the plants in an endophyte form, as an entomopathogen reservoir. (Rehner et al., 2006).

Amongst the insect pathogen group, fungi have a very particular feature: they are not required to be ingested by the insect to prompt disease, given they can directly penetrate through the host's cuticle. Their growth and development is primarily limited to environmental conditions, especially high humidity and adequate temperature, depending on the fungus.

Fungi reproduction units are known as spores or conidia. Insects are usually infected by these reproductive units. The infection process can be divided in three steps: 1) adhesion and spore germination in the insect's cuticle; 2) penetration within the insect's hemocele; and 3) fungi development, generally ending with the insect's death (Tanada and Kaya, 1993).

Spores must make contact with the insect's cuticle. It has been observed that a hydrophobic interaction is initially produced between the spore and the cuticle surface evidenced by the secretion of an adhesive mucous substance as the spores increase in size in the pregermination process. This substance allows it to adhere to the cuticle (Boucias and Pendland, 1991). The insect may avoid infection in its cuticle if the medium does not provide the essential factors for adhesion to take place and for the spore to develop. Specifically, infection may be avoided due to low humidity, the impossibility for the fungus to use the available nutrients in the insect's cuticle, or because the necessary factors are not established which allow for the acknowledgement of a susceptible host or penetration at the infection site (St. Leger, 1991). In some cases, the fungus penetrates the insect through its natural openings (mouth, spiracles). The penetration mode depends on the insect's cuticle properties.

After the spore is able to attach itself to the cuticle and is not inhibited, it germinates, differentiates and forms a germ tube which works as a penetration hypha or it forms an appressorium which through a physical force creates mechanical pressure. The foregoing together with the production of chemical substances such as enzymes, break the insect's cuticle in such a way that the hyphae penetrate the cuticle and enter the insect body cavity.

Entomopathogenic fungi possess a wide variety of mechanisms which allow breaking and assimilating host materials and overcoming resistance mechanisms. Fungi must produce substances which allow for insect cuticle degradation, substances which inhibit specific insect processes and substances which interfere with the insect's regulatory system. These substances not only refer to enzymes but toxins have also been reported (Hajek and St. Leger, 1994).

Amongst fungi virulence determining enzymes we find the Pr1 protease of *Metarhizium anisopliae* (St. Leger et al., 1992), whose expression is produced upon cuticle penetration leading to degradation of proteins present in the cuticle. Over-expression of this protein in genetically engineered *M. anisopliae* (St. Leger et al., 1996), and in *Beauveria bassiana* transformed with the gen this protein expresses (Góngora, 2004; Rodríguez and Góngora, 2005), prompted an increase in virulence of these fungi. As for *B. bassiana* infecting *Hypothenemus hampei*, the increase in virulence stood at about 30% in comparison to non-transformed original strains.

Regarding toxins, in certain cases their importance in pathogenicity processes has not been clear (Gillespie and Claydon, 1989). However, as for *M. anisopliae*, the production and concentration of the destruxin toxin, a cyclodepsipeptide, in certain strains is related with fungi virulence processes (Kershaw et al., 1999). Other reported toxins correspond to beauvericin, in *B. bassiana*, which have been found related to *H. hampei* larvae mortality (Arboleda et al., 2003 y 2011). It has also been reported in *Verticillium*, now *Lecanicillium*, the bassianolide toxin (Kanaoka et al., 1978). It is believed that many of these toxins also have a bactericide effect preventing bacterial putrefaction of insects, which allows for fungi growth and insect modification (McCoy et al., 1988).

Studies carried out by Freimoser et al. (2005), on entomopathogen-insect interaction using microarrays and extensive gene sequence groups, indicate that *M. anisopliae* is capable of infecting a broad group of insects. Proteins involved in cuticle degradation (protease), transport proteins and proteins related to transcription regulation are reported, as well as many genes with unknown function. Likewise, the repression of many other proteins is evidenced. Gene expression patterns in response to growth on the cuticle of other types of insects, such as cockroaches (*Blaberus giganteus*) and coleoptera (*Popillia japonica*), is different to that observed in Lepidoptera, indicating that the entomopathogen responds specifically and precisely against each insect and environmental condition using a wide spectrum of gene machinery.

Once the fungus has penetrated the cuticle, it goes on to the hemocele, wherein the hyphae convert into hyphael bodies or blastospores and/or protoplasts. These then disseminate to all parts of the insect body and ultimately destroy the internal organs. The insect's death occurs due to nutritional deficiencies, invasion and destruction of insect tissue and metabolic imbalances due to toxic substances which are produced by the fungus (Gillespie y Claydon, 1989).

Within the insect's cavity, infection success will depend on the genetic potential the fungus has to grow rapidly, penetrate barriers found inside the insect and resist toxic substances the insect might produce, as well as its defense mechanisms. The insect's primary defense mechanism is the encapsulation and melanization of foreign bodies.

Once the insect's immune barriers are overcome, fungi grows saprophytically, forms a mycelium mass and produces reproductive structures within the hemocele. The spores and sterile hyphae emerge from the insect under adequate humidity and temperature conditions. The spore production, unloading, dispersion, survival and germination processes will depend on environmental conditions. The vast number of spores produced by the insect cadavers partially compensates the high odds of the great majority of them not surviving at all (Hajek y St Leger, 1994).

The *Beauveria bassiana* (*Ascomycota: Hypocreaes*) fungus is the entomopathogen species most widely marketed worldwide against a number of pests. Formulations consist of conidia, in powder form, in order to be resuspended in water and emulsion oils. Its use in commercial crop fields in Brazil has been reported for the control of the banana root borer (*Cosmopolites sordidus*) (Alves et al., 2003), and in China for the control of Lepidoptera pests (*Dendrolimus* sp.), in pine tree fields (Feng 2003). It is estimated that in China 10,000 tons of *B. bassiana* conidia were produced and applied for several decades for agricultural and forest field pest control (Feng et al., 1994).

In Colombia, this fungus was recorded battling coffee berry borer as soon as it made its entry in the southern part of the country (Vélez and Benavides, 1990). It is a natural control for this coffee pest found infecting the insect in practically all countries where it has been dispersed. This fungus is part of the comprehensive management strategy against coffee berry borer and its use is recommended by the FNC-Cenicafe (Bustillo et al., 1998; Bustillo, 2004). For coffee berry borer control in 1992, 5 tons of fungi were used and in 1998 this was increased to 300 tons, selecting the most virulent strains (Bustillo, 2002).

Coffee berry borer *Hypothenemus hampei* (Ferrari) (Coleóptera: Scolytidae), originated in equatorial Africa and was first reported in Colombia in 1988. It is considered the utmost pest in Colombian coffee farming. The insect females stand on the coffee berry and perforate it until reaching the inside, where eggs are deposited. These eggs emerge and the larvae feed off the seed, making for a loss in berry weight, quality reduction and small berry drops (Duque et al., 2000). The insect inflicts harm when perforating the berry and internally reproducing itself within the endosperm causing total loss of the bean, wherein it can lay anywhere between 25 and 150 eggs, remaining inside all this time and reaching 2 to 4 generations if no timely control measures are taken. Due to the high coffee berry borer's reproductive rate, and its internal feeding habit off the coffee fruit, coffee berry borer control using traditional contact insecticides become a difficult task (Cárdenas, 1991, Villalba et al. 1995, Bustillo 2002).

Normally, coffee fruits start to become susceptible to coffee berry borer when its dry weight is 20% or more, reachable when the fruit is 100 to 150 days into its development after flowering (pollination), depending on the latitude (Le Pelley 1968; Montoya y Cárdenas 1994).

Studies on coffee berry borer dispersion have demonstrated that ground infested fruits which have fallen as a consequence of an insect attack or from crop agronomical activities become population reservoirs and represent the primary insect dispersion site.

The *B. bassiana* fungus is considered a natural control for the insect. As for the Colombian coffee ecosystem, the use of this fungus is a friendly alternative from an environmental standpoint for controlling the insect, especially considering the effect of the insecticides in this ecosystem, wherein the coffee farmer actually lives on site. The natural control prompted by the fungus within the coffee zone (10%) (Cárdenas et al., 2007), in part is due to massive applications fostered by Cenicafe (Bustillo, 2002). Therefore, if the fungus were not causing this effect on the pest populations, Colombian coffee farming losses would be even greater.

Cenicafe currently holds a *B. bassiana* culture collection comprising 117 isolations, obtained from coffee berry borer and other insects, stemming from Colombia and other countries. Access to strains isolated by Cenicafe is carried out through a material transfer agreement directly contacting Cenicafe at (www.cenicafé.org, Sede Planalto—Km. 4 via Chinchiná, Manizales (Caldas)—Colombia; Tel: +57(6) 8506550; Fax: +57(6)8504723—+57(6)8506630—+57(6) 8507561). These strains have been evaluated for the past 15 years for their virulence features against coffee berry borer and their genetic diversity (Góngora et al. 2009). Research carried out at Cenicafe has demonstrated that not all *B. bassiana* strains are alike and control coffee berry borer in the same proportion. Within Cenicafe's culture collection, there are more virulent strains than others. Hence, using the same amount of spores, some strains inflict greater mortality on coffee berry borer (Cruz et al., 2006).

In order to obtain better efficacy from biocontrolling fungi, further study has been undertaken in genetic mechanisms that provide these fungi their pathogenicity and virulence characteristics. The use of blends of strains with other bio-controlling agents has already been reported in biological control. These types of blends not only increase the spectrum of action but also assure its action under different environmental conditions (Góngora, 2008). Inglis et al. (1997) determined that a blend of *B. bassiana*, due to its resistance to low temperatures, and *M. anisopliae*, due to its resistance to high temperatures, could be more effective for controlling grasshoppers than using these strains separately.

Vergel, et al., (2010) discloses a study on the compatibility of two entomopathogenic fungi (*Beauveria bassiana* and *Paecilomyces fumoroseus*) in combination with a blend of chili and garlic extracts and predator dust mites, particularly *Phytoseiulus persimilis* and *Neoseiulus californicus*, on the red spider *Tetranychus urticae*, considered one of the major rose pests. This study evaluated 20 treatments including three fungus concentrations, three concentrations of the garlic and chili combined extract, fungi combinations and the plant extract and two controls. It was reported that no difference existed in the mortality rate of the dust mite between treatments, but on the other hand, there was an effect on *N. californicus* fertility. Additionally, 11 treatments on roses were evaluated in order to determine the effect of releasing the predator dust mites and the further combination of entomopathogenic fungi with plant extracts. It was concluded that the most effective treatment was the release of just *P. persimilis*. However, the release of *N. californicus* followed by spraying the entomopathogenic fungus over the top third of the rose had a notorious effect.

Cruz et al., (2006) evaluated the use of strain blends regarding *B. bassiana* virulence when facing coffee berry borer. Several strains of this fungus were genetically characterized using ITS, beta-tubulin sequences and AFLPs, grouping the isolates in 3 genetic groups. Virulence assays of the isolates when facing coffee berry borer using $1 \times 10^6$ conidia/ml concentrations showed that virulence obtained for each strain fluctuated between 57.5% and 89.1%. When mixing genetically different strains and with virulence in excess of 82%, significantly low mortalities were obtained (57%). However, when blending genetically different strains (Bb9001, Bb9119, Bb9024) with virulence under 80%, the greatest percentages of mortality were obtained. Both synergic as well as antagonistic effects were observed with respect to virulence, the latter combination being promising as an alternative to evaluate on the field. Through AFLPs it was confirmed that strains may co-infect the insect. The use of blends is evidenced as an alternative in lieu of the use of one sole strain for insect control and a window opened for the development of future composite compounds.

Furthermore, it was corroborated that the blend of strains which individually show low virulence (Bb9001, Bb9119, Bb9024), caused high mortality (100%) on coffee berry borer in lab tests, i.e., low virulence strains when blended produce high virulence. In field tests, artificial infestations were performed using the insect towards tree limbs observing a 66.6% mortality rate. From a biological standpoint, a mortality rate near 70% on this insect is an important result which indicates it is possible to increase the entomopathogen's efficacy (Cárdenas et al. 2007).

Vera et al. (2010) evaluated amongst separate trees covered by a cage, the effect of *B. bassiana* strains on 50 infested fruits left on the ground and their impact on infestation among fruits still on the plant, in two experimental stations (Naranjal, Caldas and Paraguaicito, Quindio) in the Colombian coffee zone. The evaluated strains were as follows: Bb9205, Cenicafe's blend of strains (Bb9001, Bb9024 y Bb9119) and a commercial formulation sprayed at a concentration of $1 \times 10^9$ conidia per tree over 50 infested fruits per tree plate. At 30 days, all strains reduced the levels of coffee berry borer in the trees; the blend of strains reduced the infestation between 50% and 30% for both stations. The mortality rate of coffee berry borer in dissected fruit of each treated tree was over 40% in comparison to a 15% mortality rate in the control group without the application of fungi. The B. bassiana strains reduced anywhere between 55 and 75% of insect populations within new infested fruit towards the top of the plant, the Cenicafe blend of strains being the most effective. The results show that B. bassiana significantly reduces the coffee berry borer population which emerges from infested fruits on the ground and reduces future insect generations.

As to the use of M. anisopliae, Milner and Lutton (1976) reported that this fungus is better adapted to ground conditions than B. bassiana, thus used widely in pest control at a rhizosphere level, whilst B. bassiana is better associated to pests in the aerial or top part of plants. Therefore, as to coffee berry borer population control in the ground, it results logical to assume that M. anisopliae could be a good control. Hence, Jaramillo (2012) evaluated the effect of M. anisopliae in field conditions and in combination with the foregoing B. bassiana strain blends, validating the effect of these blends in a commercial coffee crop field in Pereira, Risaralda (Colombia). In a random block design using 120 trees per treatment, four treatments were applied including a control, on coffee berry borer populations which had emerged in fruits left at the tree plates, prior to treatment spraying. Applications were performed every 20 days between September and December 2011. The effect of the blends was also evaluated on the new borer generations in lab assays. The Ma9236 strain and the "Cenicafe" strain blend (Bb9001, Bb9024, Bb9119) and "Cenicafe" plus Ma9236 were effective reducing the levels of infestation in trees anywhere between 18 to 47% in comparison to the control. The use of a blend with different action spectra under environmental conditions indicates it is possible to maintain the borer percentage in the lot under 6.6%. In the laboratory, the "Cenicafe" B. bassiana blend was able to affect the capacity of borer's egg laying in 87%, indicating that the blends of strains aside from increasing mortality in borer populations, also directly affect new generations.

Use of Botanical Repellents in Insect Control

Several products exist made from plant extracts coming from the Liliaceae and Solanaceae families, through a process allowing high purity and concentration. This is the case for the product CapsiAlil® developed by Ecoflora in Medellin, Colombia (according to information available in http://www.ecofloragro.com/images/stories/pdf/ficha capsialil.pdf search made 10 Oct. 2012), whose active ingredients are 54.2% Liliaceae family and 43.4% Solanaceae family. CapsiAlil® is a plant extract for agricultural use, having a repellent and insecticide effect. Its irritating effect on pest insects and mites increases its mobility and vulnerability on other management tools. It proves ideal for combining it with comprehensive pest management programs due to its high compatibility and synergy with biological and chemical reagents. It has been used in comprehensive pest management including mites, trips (Thrips sp.), colaspis (Colaspis sp.), grass bugs (Collaria sp.) and weevils such as Rhynchophorus palmarum and Anthonomus grandis.

Its use is recommended as a standalone or in a blend with biological or chemical insecticides and acaricides directed towards the foliage or ground in flower crop fields (chrysanthemums, rose, carnation, African daisy, aster, hydrangea, liatris, lily), fruit fields (citric, grape, avocado, granadilla, passion fruit, banana, blackberry), ornamental, foliage, vegetables (asparagus, tomato, peppers, chili, beans, broccoli, cauliflower) and grasses, in clean agriculture programs, under Best Agricultural Practices (BAP) or ecological agriculture (EcoFlora 2005). Several field tests have demonstrated that applying CapsiAlil® alone (1.0 cc/L) or mixed with insecticides (0.3 cc/L y 0.5 cc/L), generates excellent control over thrips populations, thanks to cuticle degradation of the immature stages and the repellent and irritating properties of its active ingredients which prompt the insects to exit their refuges thus increasing their mobility, exposure and vulnerability when facing biological and chemical products which act on contact (EcoFlora 2005).

Pest insect and plant pest pathogen fungi have historically not reached the control expectations due in part to their mortality tardiness, failure in identifying active strains at low dosages and inconsistencies in results in comparison to chemical insecticides, with whom they compete (Gressel et al., 2007a,b). These failures can be further aggravated due to the incomplete understanding of the biological and genetic factors which make a fungus effective. However, the lack of efficacy may also be predetermined due to the fact that evolutionary balances may have developed amongst microorganisms and their hosts in such a manner that the rapid death of insects, even at high dosages is not a feature which favors the pathogen's adaptation. In this case, effective biocontrol from a cost standpoint would require gene transfer to the fungus (Gressel et al. 2007a), or the combination thereof with some other strategy which would allow to overcome the above disadvantages.

Furthermore, the use of botanical compounds is also limited due to the variations in response to these substances within a same insect species; even much related species may differ dramatically in their behavior against a certain substance. The second aspect is the rather large plasticity also with regards to behavior which insects demonstrate; many may rapidly adapt to a substance which initially could have been repellent, changing its effect in a short period of time.

3. DESCRIPTION OF THE FIGURE

FIG. 1 (A and B). Experimental unit. 50 fruit branch having coffee berry borer and sprayed with CapsiAlil® together with the Beauveria bassiana fungus. A: Absolute control. B: treatment with B. bassiana and CapsiAlil® (observe the presence of the white-colored fungus towards the penetration points of the borer in the fruits).

4. BRIEF DESCRIPTION OF THE INVENTION

The present invention provides a natural pesticide formulation for the control of coffee berry borer (Hypothenemus hampei) in coffee plants, and likewise of other insects of economical importance in corn crop fields and greenhouse crop fields (flowers and vegetables), containing A and B elements, wherein A corresponds to botanical products having an insect repellent effect and B consists of an entomopathogenic fungus strain or a blend of entomopathogenic fungi strains specific for arthropod control.

5. DETAILED DESCRIPTION OF THE INVENTION

A natural pesticide formulation was developed for the control of coffee berry borer (Hypothenemus hampei) in coffee plants, and likewise of other insects of economical importance in corn crop fields and greenhouse crop fields (flowers and vegetables), containing A and B elements, wherein A corresponds to botanical products having an insect repellent effect and B consists of an entomopathogenic fungus strain or a blend of entomopathogenic fungi strains specific for arthropod control.

Amongst the entomopathogens, the following species are found:

*Beauveria* sp, *Metarhizium* sp., *Paecilomyces* sp., *Lecanicillium* sp., *Nomuraea* sp., *Isaria* sp., *Hirsutella* sp., *Sorosporella, Aspergillus* sp., *Cordiceps* sp., *Entomophthora* sp., *Zoophthora* sp., *Pandora* sp., *Entomophaga* sp., *Conidiobolus* and *Basidiobolus.*

Amongst the botanical products having an insect repellent effect, the following are found:

*Melia azedarach* (Meliaceae): White cedar, a.i. triterpenoids

*Azadirachta indica* (Meliaceae): Nimtree, a.i. Azadirachtin and derivatives thereof (Triterpenoids, limonoids, Nimbina, Salannina).

*Allium sativum* (Alliaceae): garlic. a.i. alliina, allinase, allicine.

*Capsicum* sp. (Solanaceae) including *Capsicum annuum, Capsicum frutescens, Capsicum chinense* and *Capsicum pubescens*: chili peppers. a.i. Capsicine.

*Lonchocarpus utilis* (Leguminosae): rotenone. a.i. Rotenone.

*Chrysantemum cinaerifolium* (Compositae): chrysanthemums. a.i. Piretrine and its ester components, formed by the combination of chrysanthemic acid and pyretric acid and the piretrolone, cinerolone and jasmolone alcohols.

*Nicotiana tabacum* (Solanaceae): tobacco. a.i. nicotine.

*Riania speciosa* (Flacourtiaceae): Ryanodine. a.i. Ryanodine.

*Polygonum hydropiper* (Polygonaceae): water pepper. a.i. Polyglodial.

*Citrus* sp. (Rutaceae): lime, citric fruits. a.i. limonoids.

*Artemisia annua* (Asteraceae): sweet wormwood. a.i. Artemisina.

*Equinacea angustifolia* (Asteraceae): Echinacea. a.i. echinicine.

*Hyssopus officinalis* (Lamiaceae): Hyssop. a.i. cíñelo, b-pinene and various monoterpenes such as L-pinocanfene, isopinocanfone and pinocarivon.

*Lavandula officinalis* (Lamiaceae): Lavender. a.i. linalol, eucaliptol, and borneol

*Mentha pulegium* (Lamiaceae): a.i. pulegone, menthol and other terpenic substances such as Menton, isomentone.

*Ocimun basilicum* (Labiatae): Basil. a.i. linalol, estregol, leneol.

*Artemisia vulgaris, Ambrosia cumanenses* (Asteraceae): artemis. a.i. Ciñelo.

*Salvia officinalis* (Lamiaceae): Salvia. a.i. boreol, cineol, tuyona.

*Robinia seudoacacia* (Fabaceae): false acacia (black locust). a.i. lectin.

*Rosmarinus officinalis* (Lamiaceae): Rosemary. a.i. phenolic acids (cafeic, chlorogenic, rosmarinic), flavonoids (luteol and epigenol derivatives), Diterpenos (carnosol, rosmanol, rosmadial).

*Tagetes patula* (Asteraceae): French marigold. a.i. thiofenes, such as α-terthienyl and 5-(3-butene-1-inyl)-2, 2'-bitienyl (BBT).

*Melissa officinalis* (Lamiaceae): lemon balm. a.i. linalol.

*Urtica*sp. (Urticaceae): urtica. a.i. serotonin, histamine, phylosterine

*Ruta graveolens* (Rutaceae): rue. a.i. Rutin, inulin.

*Canavalia ensiformis* (Fabaceae): Canavalia. a.i. Canavalin.

*Cymbopogon nardos*: Citronella. a.i. citronelal and geraniol, I-limonene, canfene, dipentene, citronelol, borneol, nerol, metileugenol.

*Mentha spicata* (Lamiaceae): spearmint. a.i. menthol, phelandrene, centene.

*Artemisia absinthium* (Asteraceae): wormwood, green ginger. a.i. cineol, tuyona.

*Ocimum basilicum* (Lamiaceae): basil. a.i. linalol, estregol, leneol.

*Calendula otticinalis* (Asteraceae): marigold. a.i. caléndulíne.

*Minthostachys mollis* (Lamiaceae): Muña, Peperina. a.i. Mentol, mentola.

*Mentha piperita* (Lamiaceae): peppermint. a.i. menthol, ciñelo.

*Moringa oleifera.*

*Tephrosia purpurea*

EXAMPLE 1

The capacity of prompting repellence and mortality on coffee berry borer was tested in field conditions using the combination of the botanical product CapsiAlil®, which contains garlic extract (*Allium sativum*) and chili peppers (*capsicum*), with the *Beauveria bassiana* fungus blends. For this, the following treatments were tried: CapsiAlil® (at five different concentrations) was combined with the low virulence strains of the *Beauveria bassiana* fungus (Bb9001, Bb9119, Bb9024), but upon mixing achieve high virulence, at a fungus concentration of $2\times10^{10}$ spores/liter. The botanical product was also evaluated at the same 5 concentrations, the fungus at a $2\times10^{10}$ spores/liter concentration and an absolute control (distilled water) (treatments identified in Table 1).

TABLE 1

Treatment description for each product.

| Treatment | Fungus concentration:CapsiAlil ® concentration |
|---|---|
| 1 | 0:0.03% |
| 2 | 0:0.3% |
| 3 | 0:3% |
| 4 | 0:6% |
| 5 | 0:10% |
| 6 | $2 \times 10^{10}$ sp/L:0.03% |
| 7 | $2 \times 10^{10}$ sp/L:0.3% |
| 8 | $2 \times 10^{10}$ sp/L:3% |
| 9 | $2 \times 10^{10}$ sp/L:6% |
| 10 | $2 \times 10^{10}$ sp/L:10% |
| 11 | $2 \times 10^{10}$ sp/L:0.03%:0 |
| 12 | 0:0 |

The treatments were sprayed in parcels holding *Coffea arabica* Colombian variety 2.5 year old trees, in productive branches holding 120-140 day developed fruits, previously infested with coffee berry borer. The experimental unit was made up of one tree. Each treatment (concentrations and absolute control) comprised 15 experimental units statistically determined variance of 142 associated to the emerging borer average; minimum acceptable difference of 10 borer; greater than 90 reliability and a significance level of 5%.

The experimental units were assigned to the treatments according to the completely random experimental design, and one daily repetition was performed. For each treatment, one branch from the productive zone was randomly taken and all perforated fruits were withdrawn, leaving 50 fruits on the branch. Furthermore, the selected branch was covered using a cylindrical entomological sleeve made from No. 10 caliber wire, 40 cm long and 20 cm diameter, wrapped in white muslin fabric, being fixed to the branch through a polypropylene thread. These sleeves had a window sown in with a Velcro 180° diameter closing along the sleeve in order to visualize the borer emerging behavior. Once the entomological sleeves were installed, infestations in the branch inside the sleeve with 100 borer adults provided by the Biocafe lab were performed. Furthermore, the sleeves were closed with a polypropylene thread and were fastened to the top branch in order to maintain it horizontal. After 24 hours post-infestation, borers were removed, the number of perforations in each infested fruit was recorded and treatment was applied guaranteeing the entire coverage of the branch. For the application, a 1.6 capacity Royal Condor 15-25 pressure accumulation spray unit and a TXVK-3 nozzle (100 cc/min flow at 25 psi) was used.

After each spray, the number of emerging borers from the infested fruits was recorded during 5 minutes of direct observation on each branch. Counting was done through the window.

The emerging percentage was estimated as the result from dividing the number of borers emerged from each branch by the number of total perforations per branch. The window was then closed and the sleeve was left tied to the branch for 20 days.

20 days after spraying the treatments, the number of adult borers (live and dead) was recorded in each experimental unit. For this to happen, all infested fruits were removed from each branch and deposited in refrigerators inside marked plastic bags in order to be dissected in the lab under a stereoscope. Borer biological status was recorded in each perforated fruit.

Table 2 shows the results of the repellence effect evaluation with regards to the emerging variable caused by the different treatments.

TABLE 2

Percentage of Borer emergence, 3 days after treatment application.

| | Treatment | % emergence | EE |
|---|---|---|---|
| 1 | Capsi 0.03% | 5.23 | 2.2 |
| 2 | Capsi 0.3% | 5.10 | 2.6 |
| 3 | Capsi 3% | 6.31 | 1.8 |
| 4 | Capsi 6% | 9.27 | 2.3 |
| 5 | Capsi 10% | 16.18* | 3.3 |
| 6 | Capsi 0.03% + Bb | 6.21 | 1.8 |
| 7 | Capsi 0.3% + Bb | 5.34 | 2.1 |
| 8 | Capsi 3% + Bb | 4.85 | 2.4 |
| 9 | Capsi 6% + Bb | 7.67 | 3.1 |
| 10 | Capsi 10% + Bb | 15.67* | 2.5 |
| 11 | Bb (relative control) | 5.27 | 2.1 |
| 12 | Absolute control | 5.23 | 2.3 |

*Significantly different average with respect to the TA absolute control

The results showed statistical differences between treatments (5% ANOVA -P<0.05). A treatment effect was evidenced when 10% of the botanical product was used, both blended with *B. bassiana* or alone, according to the comparison test with the absolute control (5% Dunnett test).

Table 3 shows the mortality results on coffee berry borer caused by the different treatment over 20 days. The adult borer mortality obtained in the field after applying the botanical product and the fungus suggest a synergy effect, wherein both the botanical product as well as the fungus inflicted borer mortality of about 45% when applied individually, but when combined, reached a mortality rate in excess of 70%. This evidenced an additive effect causing an additional 30% mortality in coffee berry borer due to the effect of both products.

TABLE 3

Percentage of dead adult borers, 20 days after applying treatments during the repellence assay.

| | Treatment | n | Average % mortality | EE |
|---|---|---|---|---|
| 1 | Capsi 0.03% | 40.80 | 21.07 | 4.50 |
| 2 | Capsi 0.3% | 37.50 | 23.74 | 2.20 |
| 3 | Capsi 3% | 37.30 | 38.63* | 6.65 |
| 4 | Capsi 6% | 39.56 | 32.36 | 4.58 |
| 5 | Capsi 10% | 37.44 | 45.61* | 5.91 |
| 6 | Capsi 0.03% + Bb | 37.20 | 36.62* | 7.27 |
| 7 | Capsi 0.3% + Bb | 41.40 | 42.47* | 5.30 |
| 8 | Capsi 3% + Bb | 40.20 | 51.60* | 5.48 |
| 9 | Capsi 6% + Bb | 36.70 | 50.15* | 6.71 |
| 10 | Capsi 10% + Bb | 35.78 | 74.05* | 4.29 |
| 11 | Bb (relative control) | 42.10 | 43.52 | 4.54 |
| 12 | Absolute control | 43.50 | 15.09 | 2.64 |

*Significantly different average with respect to the TA absolute control

The invention claimed is:

1. A pesticide formulation consisting of elements A and B, wherein:
    A is selected from the group consisting of extracts of: garlic or *Allium sativum*, and chili pepper, *Capsicum sp, Capsicum anuum, Capsicum chinensen*, or *Capsicum pubescens*; and garlic or *Allium sativum*, and chili pepper, *Capsicum sp, Capsicum anuum, Capsicum chinensen*, or *Capsicum pubescens*, and absinthe, *Artemisia sp, Artemisia annua*, or *Artemisia vulgaris*; and
    B is entomopathogenic fungi *Beauveria bassiana*; wherein the *Beauveria bassiana* is selected of the group consisting of strains Bb-9001, Bb-9024 and Bb-9119, or blends thereof.

2. The pesticide formulation according to claim 1, wherein the blend of strains has a $2 \times 10^{10}$ spore/L concentration.

3. The pesticide formulation according to claim 1, wherein A is found in a 0.01% to 20% total weight proportion of the formulation.

4. The pesticide formulation according to claim 3, wherein the blend of strains has a $2 \times 10^{10}$ spore/L concentration.

5. The pesticide formulation according to claim 1, wherein A is found in a 10% total weight proportion of the formulation.

6. The pesticide formulation according to claim 5, wherein the blend of strains has a $2 \times 10^{10}$ spore/L concentration.

7. The pesticide formulation according to claim 1, wherein the blend of *Beauveria bassiana* fungus strains is a blend of Bb-9001, Bb-9024 and Bb-9119 strains.

8. The pesticide formulation according to claim 7, wherein the blend of strains has a $2 \times 10^{10}$ spore/L concentration.

9. A kit comprising a pesticide formulation consisting of elements A and B, wherein:
    A is selected from the group consisting of extracts of: garlic or *Allium sativum*, and chili pepper, *Capsicum sp, Capsicum anuum, Capsicum chinensen*, or *Capsicum pubescens*; and garlic or *Allium sativum*, and chili pepper, *Capsicum sp, Capsicum anuum, Capsicum chinensen*, or *Capsicum pubescens*, and absinthe, *Artemisia sp, Artemisia annua*, or *Artemisia vulgaris*; and B is entomopathogenic fungi *Beauveria bassiana*;
wherein the *Beauveria bassiana* is selected of the group consisting of strains Bb-9001, Bb-9024 and Bb-9119, or blends thereof.

\* \* \* \* \*